United States Patent [19]

Hayes et al.

[11] Patent Number: 4,562,063

[45] Date of Patent: Dec. 31, 1985

[54] ASTRINGENT GEL DENTIFRICE

[75] Inventors: Harry Hayes, Warrington; Kenneth Harvey, Wilmslow, both of England

[73] Assignee: Colgate-Palmolive Company, New York, N.Y.

[21] Appl. No.: 680,426

[22] Filed: Dec. 11, 1984

[51] Int. Cl.$^4$ .............................................. A61K 7/16
[52] U.S. Cl. ...................................................... 424/49
[58] Field of Search ..................................... 424/49–58

[56] References Cited

U.S. PATENT DOCUMENTS

| | | | |
|---|---|---|---|
| 3,538,230 | 11/1970 | Pader et al. | 424/50 |
| 3,728,446 | 4/1973 | Roberts et al. | 424/49 |
| 3,932,606 | 1/1976 | Barth et al. | 424/52 |
| 3,939,261 | 2/1976 | Barth | 424/49 |
| 4,022,880 | 5/1977 | Vinson et al. | 424/49 |
| 4,082,841 | 4/1978 | Pader | 424/50 |
| 4,100,269 | 7/1978 | Pader | 424/49 |
| 4,138,477 | 2/1979 | Gaffar | 424/52 |
| 4,144,323 | 3/1979 | Lamberti | 424/54 |
| 4,153,680 | 5/1979 | Seybert | 424/49 |
| 4,160,821 | 7/1979 | Sipos | 424/49 |
| 4,339,432 | 7/1982 | Ritchey et al. | 424/54 |
| 4,396,599 | 8/1983 | Sipos | 424/52 |
| 4,416,867 | 11/1983 | Ritchey et al. | 424/49 |
| 4,425,325 | 1/1984 | Ritchey et al. | 424/54 |
| 4,435,380 | 3/1984 | Pader | 424/49 |
| 4,456,585 | 6/1984 | Hayes et al. | 424/49 |
| 4,469,674 | 9/1984 | Shah et al. | 424/52 |

FOREIGN PATENT DOCUMENTS 2038303 7/1980 United Kingdom .
1572864 8/1980 United Kingdom .

Primary Examiner—Shep K. Rose
Attorney, Agent, or Firm—Robert L. Stone; Herbert S. Sylvester; Murray M. Grill

[57] ABSTRACT

Astringent gel dentifrice containing a water-soluble zinc salt, a hydrous silica gel polishing agent compatible and substantially non-reactive with the zinc salt and alkali metal carboxymethyl cellulose.

10 Claims, No Drawings

ASTRINGENT GEL DENTIFRICE

This invention relates to a gel dentifrice containing a water-soluble zinc salt which provides an astringent effect on oral mucosa and periodontal tissue during toothbrushing with a compatible gelling agent.

The astringent effectiveness of zinc ions provided by water-soluble zinc salts to promote and improve oral hygiene has long been known. Nevertheless, there have been limits on the practical use of zinc in dentifrice compositions since zinc ions can readily react with typical dentifrice components causing substantial loss of availability of zinc ions.

For instance, nonionic gelling agents such as hydroxyethyl cellulose have been preferably used in dentifrices when water-soluble zinc salt is employed. When alkali metal carboxymethyl cellulose has been employed in the presence of zinc ions, reaction occurs removing zinc ions leading to possible gel breakdown and phase separation. In U.S. Pat. No. 3,728,446, to Roberts et al, the in situ reaction between zinc ions and alkali metal carboxymethyl cellulose to form visible particles is described.

It has therefore been difficult to prepare dentifrices containing amounts of zinc ions which remain effective in providing astringent properties in the presence of alkali metal carboxymethyl cellulose. Furthermore, gel-type dentifrices providing zinc astringency have not been available due to the incompatibility of zinc ion with various siliceous polishing agents.

In the applicants' co-pending application for "Astringent Dentifrice" filed on the same day herewith, a precipitated, amorphous silica gel is compatibly employed with zinc ions, which silica gel has been described in British Published Patent Application No. 2 038 303 A to Feig et al and in co-pending commonly assigned U.S. patent application Ser. No. 576,046, filed Feb. 1, 1984. Such material is available from Grace G.m.b.H. as product such as Syloblanc 81, Syloblanc 81C and Syloblanc 82. It is distinct from the type of xerogels which have been sold by W. R. Grace & Co. under the trademark Syloid and which are particularly described in U.S. Pat. No. 3,538,230 to Pader et al. Indeed, although some products sold by Grace G.m.b.H. under the trademark Syloblanc were formerly or are still available under the trademark Syloid, none of Syloblanc 81, Syloblanc 81C or Syloblanc 82 have ever been available under the trademark Syloid. It is particularly noteworthy that the grades of the silica gel employed in the present invention are less abrasive as the surface area increases whereas the grades of silica xerogel which are described in U.S. Pat. No. 3,538,230 are generally more abrasive as their surface area increases.

In view of the low compatibility of most polishing agents with zinc, including those polishing agents of U.S. Pat. No. 3,538,230, it was quite unexpected that a particular siliceous polishing material would not have such a problem and that further, in the presence of such polishing agent, the reaction between zinc ions and alkali metal carboxymethyl cellulose is substantially reduced. Thus, in accordance with the present invention, it has been found that retention of high levels of astringency from zinc ions is attained when such particular siliceous polishing material and alkali metal carboxymethyl cellulose are employed.

It is an advantage of this invention that an astringent gel dentifrice containing zinc ions and a carboxymethyl cellulose gelling agent is provided.

It is a further advantage of this invention that an astringent gel-type toothpaste containing zinc ions and a carboxymethyl cellulose gelling agent is provided.

Further advantages of the invention will be apparent from considerations of the following specification.

In accordance with certain of its aspects, this invention relates to an astringent gel dentifrice comprising about 20–90% by weight of liquid vehicle comprising water in amount of at least about 3% by weight of said dentifrice, about 0.05–5% by weight of an alkali metal carboxymethyl cellulose gelling agent and about 10–50% by weight of a polishing agent comprising a synthetic precipitated, amorphous silica gel having an average particle size of 1–30 microns and (a) a surface area of 1 to 600 $m^2/g$, (b) a pore volume of 0.05 to 0.5 $cm^3/g$, (c) a product of surface area (in $m^2/g$) × pore volume (in $cm^3/g$) less than or equal to 240, (d) a calculated pore diameter of 1.5 to 2.5 nm, and (e) a water content of less than 25% by weight; and up to about 5% of a water-soluble zinc salt which provides at least about 50 ppm of zinc ions to said dentifrice.

As indicated above, the synthetic precipitated silica is of the type described in British Published Patent Application No. 2 038 303 A and U.S. patent application Ser. No. 576,046. Specific grades of the silica material described therein are suitable for use in the practice of the present invention. Further, specific grades which are particularly preferred are described in an October, 1980, trade publication of Grace G.m.b.H. of Horderstadt, Germany, as Syloblanc 81 and Syloblanc 82 as having the following typical physical and chemical characteristics:

|  | SYLOBLANC 81 | SYLOBLANC 82 |
| --- | --- | --- |
| Average particle size (according to Coulter) μm | 4 | 7 |
| Wet screen residue (42 μm) % | 0.02 | 0.02 |
| pH (5% suspension in water) | 3 | 6 |
| Surface area (B.E.T.) $m^2/g$ | 400 | 480 |
| Loss on drying % | 7 | 4 |
| $SiO_2$ content (on ignited substance) % | 96 | 99 |
| Refractive index | 1.46 | 1.46 |

In a variation of Syloblanc 81 available as Syloblanc 81C, the pH (5% suspension in water) is about 6–8.

Syloblanc 81 and 81C in particular, are highly effective in polishing dental surfaces. Syloblanc 82 is lower in polishing effect but can be used by consumers desiring such reduced effect. Likewise, grades of the silica material may be proportioned in mixtures to produce appropriate polishing characteristics. It is noteworthy that the dentifrices are compatible in unlined aluminium dentifrice tubes even in the absence of phytate salt, which is necessary in the invention described in U.S. patent application Ser. No. 576,046. The precipitated amorphous silica gel is employed in amount of about 10–50% by weight, typically about 10–40% in a gel dentifrice.

Aqueous slurries of the silica materials (e.g. about 5 to 20% slurries) typically have a pH of about 2 to 9. Since the dentifrice composition of the present invention preferably has a pH (measured in 20% aqueous slurry) of at least about 5.5, e.g. about 5.5–7.5, the pH of the dentifrice may be adjusted with an appropriate material such as sodium hydroxide, etc.

The water-soluble zinc salt is present in the dentifrice in amount of up to about 5% by weight, preferably about 0.01–3% and most preferably about 0.1–2%. Water-soluble zinc salts in accordance with the present invention are at least about 10% by weight, preferably at least about 20%, soluble in water. There is provided at least about 50 ppm of zinc ions to the dentifrice, preferably at least about 750 ppm and most preferably at least about 1000 ppm of zinc ions. Suitable zinc salts include zinc sulphate, zinc chloride, zinc bromide, zinc iodide, zinc nitrate and zinc acetate. In the case of zinc chloride, 0.01% by weight provides about 50 ppm of zinc ions and 0.2% by weight provides about 1000 ppm of zinc ions. 0.48% by weight of zinc sulphate heptahydrate provides about 1000 ppm of zinc ions. In addition, zinc oxide, a sparingly soluble (below 0.0005%) zinc compound may also be added to prevent a lowering of the pH in the product. This acts as a buffer system and improves pH stability and compatibility in unlined aluminium tubes. It may be present in amount of about 0.005–0.5% by weight.

The dentifrice comprises a liquid vehicle containing about 3–60% by weight of water, typically mixed with at least one humectant. The liquid phase comprises about 20–90% by weight of the dentifrice and is generally about 25–80% liquid, typically with about 3–50% by weight preferably about 3–10% of water in a substantially clear gel dentifrice or gel dentifrice which would be substantially clear except for the presence of an opacifying agent, such as titanium dioxide, and about 11–50% of water in a hazy to opaque gel dentifrice with about 10–90% by weight, preferably about 15–80%, of humectant. Typical humectants include glycerine, sorbitol (e.g. 70% solution), maltitol, polyethylene glycol of molecular weight of about 400–600, propylene glycol and mixtures thereof.

The dentifrice also contains an alkali metal carboxymethyl cellulose gelling or binding agent such as sodium carboxymethyl cellulose or potassium carboxymethyl cellulose, as a solid vehicle agent, in amount of about 0.05–5% by weight, typically about 0.05–2% and preferably about 0.1–1.5%. Sodium carboxymethyl cellulose gelling agent is preferred.

Any suitable surface active or detersive material may be included in the dentifrice compositions. Such compatible materials are desirable to provide additional detersive, foaming and antibacterial properties depending upon the specific type of surface active material and are selected similarly. These detergents are water-soluble compounds usually, and may be anionic, nonionic, amphoteric or cationic in structure. It is usually preferred to use the water-soluble non-soap or synthetic organic detergents. Suitable detersive materials are known and include, for example, the water-soluble salts of higher fatty acid monoglyceride monosulphate detergent (e.g. sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid materials which tends to reduce the activity of these compounds. In usual practice, the amount of such higher fatty acid material is less than 15% by weight of the amide and insufficient to substantially adversely affect it, and preferably less than about 10% of said amide material.

Other particularly suitable surface-active materials include nonionic agents such as condensates of sorbitan monostearate with approximately 20 moles of ethylene oxide, condensates of ethylene oxide with propylene oxide, condensates of propylene glycol ("Pluronic") materials and amphoteric agents such as long chain (alkyl)amidoalkylene alkalated amine derivatives, which are available under the trademark "Miranol", such as Miranol C$_2$M. Cationic surface active germicides and antibacterial compounds such as diisobutylphenoxyethyoxyethyl dimethyl benzyl ammonium chloride, benzyl dimethyl stearyl ammonium chloride, tertiary amines having one fatty alkyl group (of from 12–18 carbon atoms) and two (poly)oxyethylene groups attached to the nitrogen (typically containing a total of from about 2 to 50 ethanoxy groups per moleculae) and salts thereof with acids, and compounds of the structure

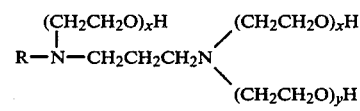

where R represents a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the oral preparation of the present invention.

Various other materials may be incorporated in the dental creams of this invention. Examples thereof are opacifiers, preservatives, stabilizers, silicones, chlorophyll compounds and ammoniated materials such as urea, diammonium phosphate and mixtures thereof. These adjuvants are incorporated in the instant compositions in amounts which do not substantially adversely affect the desired properties and characteristics and are suitably selected and used in conventional amounts.

For some purposes, it may be desirable to include antibacterial agents in the compositions of the present invention. Typical antibacterial agents which may be used in amount of about 0.01% to about 5%, preferably about 0.05 to about 1.0%, by weight of the dentifrice composition include cetyl pyridinium chloride, benzethonium chloride as well as:

$N^1$-4(chlorobenzyl-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-chlorobenzylbiguanide;
1,6-di-p-chlorophenylbiguanidohexane;
1-(lauryldimethylammonium)-8-(p-chlorobenzyldimethylammonium)5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic salts.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate, sodium saccharine, dipeptides of U.S. Pat. No. 3,939,261 and oxathiazin salts of U.S. Pat. No. 3,932,606. Suitable flavour and sweetening agents may together comprise from about 0.01 to 5% or more of the composition.

The dentifrice is packaged in a container from which it can be readily extruded. Desirably such package is a lined or unlined aluminium tube, or wax lined lead tube or plastic tube, which may be laminated with aluminium.

The dentifrice is typically prepared by forming a prefix of the gelling agent with the liquid vehicle components, e.g. water and humectant, which may also contain additional ingredients such as sweetener, and blending therewith the synthetic precipitated silica and zinc salt. If employed additional ingredients may then be added.

Although the invention is described with regard to the illustrative examples, it will be apparent to one skilled in the art that various modifications may be made thereto which fall within its scope. All amounts are by weight unless otherwise indicated.

EXAMPLE 1

The following opacified gel dentifrices are prepared and placed in unlined aluminium tubes:

|  | PARTS | |
| --- | --- | --- |
|  | A | B |
| Glycerine | 25.000 | 25.000 |
| Sorbitol (70%) | 47.050 | 43.550 |
| Sodium carboxymethyl cellulose | 0.260 | 0.260 |
| Sodium saccharin | 0.170 | 0.170 |
| Titanium dioxide | 1.000 | 1.000 |
| Water | 3.000 | 3.000 |
| Zinc sulphate heptahydrate | 0.480 | 0.480 |
| Precipitated amorphous silica gel* | 20.000 | — |
| Silica xerogel** | — | 17.000 |
| Silica aerogel*** | — | 6.500 |
| Sodium hydroxide (40%) | 0.280 | 0.280 |
| Sodium lauryl sulphate | 1.760 | 1.760 |
| Flavour | 1.000 | 1.000 |
| pH (20% slurry) | 5.9 | 6.1 |

*Syloblanc 81 available from Grace G.m.b.H.
**Syloid 63 available from W. R. Grace & Co.
***Syloid 244 thickener available from W. R. Grace & Co.

The theoretical amount of soluble zinc ions in each gel dentifrice is 1000 ppm or 0.100%.

Dentifrice A does not require the presence of thickener material to provide desirable gel character initially.

Each dentifrice is aged at room temperature and at 43° C. Both retain generally equivalent desirable consistencies. The percentage amounts of available soluble zinc ions in each dentifrice is determined to be as follows:

| | % $Zn^{+2}$ - Room Temperature | | | 43° C. | | |
| --- | --- | --- | --- | --- | --- | --- |
| | Initial | One Month | Three Months | Two Weeks | One Month | Three Months |
| Dentifrice A | 0.080 | 0.079 | 0.050 | 0.082 | 0.069 | 0.050 |
| Dentifrice B | 0.052 | 0.039 | 0.002 | 0.050 | 0.060 | 0.002 |

Dentifrice A containing Syloblanc 81 retains gel character and superior levels of soluble zinc ions compared to the otherwise generally equivalent dentifrice B containing Syloblanc 63. When the conventional 7 MXF grade of sodium carboxymethyl cellulose is employed there is phase separation and breakdown in the presence of Syloid 63 polishing agent which does not occur as much when Syloblanc 81 is employed.

It is noted that the two-week and one-month Dentifrice B evaluation levels at 43° C. reflect routine experimental variations.

Similar superior levels of retention of soluble zinc ions are attained when Syloblanc 81 of dentifrice A is replaced with Syloblanc 82 and with a 1:1 mixture of Syloblanc 81 and 82, in each, with levels of sodium hydroxide reduced or omitted with their amounts added to sorbitol (70%).

Likewise, superior retention levels of soluble zinc ions are attained when Syloblanc 81 is replaced with Syloblanc 81C, with sodium hydroxide omitted and its amount added to sorbitol (70%).

0.25 parts of zinc oxide are incorporated into each of dentifrices A and B, in place of corresponding amounts of sorbitol, thereby stabilising the pH during aging and improving compatibility with unlined aluminium tubes for prolonged periods.

EXAMPLE 2

The following stable visually clear gel dentifrices are prepared and placed in unlined aluminium tubes:

|  | PARTS | | | |
| --- | --- | --- | --- | --- |
|  | A | B | C | D |
| Glycerine | 25.000 | 25.000 | 25.000 | 25.000 |
| Sorbitol (70%) | 48.310 | 48.590 | 48.590 | 48.450 |
| Sodium carboxymethyl cellulose | 0.260 | 0.260 | 0.260 | 0.260 |
| Sodium saccharin | 0.170 | 0.170 | 0.170 | 0.170 |
| Water | 3.000 | 3.000 | 3.000 | 3.000 |
| Zinc chloride | 0.020 | 0.020 | 0.020 | 0.020 |

-continued

|  | PARTS | | | |
| --- | --- | --- | --- | --- |
|  | A | B | C | D |
| Syloblanc 81 | 20.000 | — | — | 10.000 |
| Syloblanc 81C | — | 20.000 | — | — |
| Syloblanc 82 | — | — | 20.000 | 10.000 |
| Sodium hydroxide (40%) | 0.280 | — | — | 0.140 |
| Sodium lauryl sulphate | 1.760 | 1.760 | 1.760 | 1.760 |
| Flavour | 1.000 | 1.000 | 1.000 | 1.000 |
| Blue colour solution (1%) | 0.200 | 0.200 | 0.200 | 0.200 |

Similar stability is attained when potassium carboxymethyl cellulose replaces sodium carboxymethyl cellulose.

EXAMPLE 3

The following stable hazy and opaque gel dentifrices are prepared and placed in unlined aluminium tubes:

|  | PARTS | | | |
| --- | --- | --- | --- | --- |
|  | A | B | C | D |
| Glycerine | 25.000 | 25.000 | 25.000 | 25.000 |
| Sorbitol (70%) | 24.970 | 24.870 | 24.870 | 24.870 |
| Sodium carboxymethyl cellulose | 0.700 | 0.700 | 0.700 | 0.700 |
| Sodium saccharin | 0.170 | 0.170 | 0.170 | 0.170 |
| Water | 25.000 | 25.000 | 25.000 | 25.000 |
| Zinc bromide dihydrate | 0.400 | — | — | — |
| Zinc iodide | — | 0.500 | — | — |
| Zinc nitrate hexahydrate | — | — | 0.500 | — |
| Zinc acetate dihydrate | — | — | — | 0.500 |
| Syloblanc 81C | 21.000 | 21.000 | 21.000 | 21.000 |
| Sodium lauryl sulphate | 1.760 | 1.760 | 1.760 | 1.760 |
| Flavour | 1.000 | 1.000 | 1.000 | 1.000 |

In the examples sodium cyclamte may replace sodium saccharin.

It will be apparent to those skilled in the art that further modifications of the examples illustrative of the invention may be made thereto.

We claim:

1. An astringent gel dentifrice comprising about 20–90% by weight of liquid vehicle comprising water in amount of at least about 3% by weight of said dentifrice, about 0.05–5% by weight of an alkali metal carboxymethyl cellulose gelling agent and about 10–50% by weight of a polishing agent comprising a synthetic precipitated, amorphous silica gel having an average particle size of 1 to 30 microns and
   (a) a surface area of 1 to 600 $m^2/g$,
   (b) a pore volume of 0.05 to 0.5 $cm^3/g$,
   (c) a product of surface area (in $m^2/g$) × pore volume (in $cm^3/g$) less than or equal to 240,
   (d) a calculated pore diameter of 1.5 to 2.5 nm, and
   (e) a water content of less than 25% by weight;
and up to about 5% of a water-soluble zinc salt which provides at least about 50 ppm of zinc ions to said dentifrice.

2. The astringent gel dentifrice claimed in claim 1 wherein said zinc salt is present in amount of 0.01–3% by weight.

3. The astringent gel dentifrice claimed in claim 1 wherein said zinc salt is selected from the group consisting of zinc sulphate, zinc chloride, zinc bromide, zinc iodide, zinc nitrate and zinc acetate.

4. The astringent gel dentifrice claimed in claim 3 wherein said zinc salt is zinc sulphate heptahydrate.

5. The astringent gel dentifrice claimed in claim 3 wherein said zinc salt is zinc chloride.

6. The astringent gel dentrifice claimed in claim 1 wherein said gelling agent is sodium carboxymethyl cellulose.

7. The astringent gel dentifrice claimed in claim 2 wherein said gelling agent is sodium carboxymethyl cellulose.

8. The astringent gel dentrifice claimed in claim 3 wherein said gelling agent is sodium carboxymethyl cellulose.

9. The astringent gel dentifrice claimed in claim 1 wherein said dentifrice is packaged in an unlined aluminium tube.

10. The astringent gel dentifrice claimed in claim 1 wherein said dentifrice also contains about 0.005–0.5% by weight of zinc oxide.

* * * * *